United States Patent [19]
Bergmann et al.

[11] Patent Number: 5,789,149
[45] Date of Patent: Aug. 4, 1998

[54] METHOD FOR STABILIZING OSTEOCALCIN IN HUMAN SERUM OR PLASMA SAMPLES FOR THE DETERMINATION OF THE OSTEOCALCIN CONTENT THEREIN, AND INSTRUMENTS AND SAMPLE VESSELS FOR CARRYING OUT SAID METHOD

[75] Inventors: Andreas Bergmann; Renate Weckermann, both of Berlin, Germany

[73] Assignee: B.R.A.H.M.S. Diagnostica GmbH, Berlin, Germany

[21] Appl. No.: 649,709

[22] PCT Filed: Nov. 29, 1994

[86] PCT No.: PCT/EP94/03962
§ 371 Date: Jul. 26, 1996
§ 102(e) Date: Jul. 26, 1996

[87] PCT Pub. No.: WO95/14933
PCT Pub. Date: Jun. 1, 1995

[30] Foreign Application Priority Data

Nov. 29, 1993 [DE] Germany ............ 43 40 597.5

[51] Int. Cl.[6] ............ C12Q 1/00; C12Q 1/37; G01N 33/48; G01N 33/53
[52] U.S. Cl. ............ 435/2; 435/4; 435/7.1; 435/962
[58] Field of Search ............ 435/2, 4, 7.1, 23, 435/24, 962; 530/300, 324; 422/102

[56] References Cited

U.S. PATENT DOCUMENTS 4,410,506 10/1983 Price et al. ............ 436/542
4,438,208 3/1984 Deftos et al. ............ 436/542
5,168,041 12/1992 Bergmann ............ 435/7.1

FOREIGN PATENT DOCUMENTS 557 663    9/1993  European Pat. Off. .
38 33 936  9/1989  Germany .

OTHER PUBLICATIONS

Tracy, et al: "Comparison of Monoclonal and Polyclonal Antibody–Based Immunoassays for Osterocalcin: A Study of Sources of Variation in Assay Results" Journal of Bone and Mineral Research, vol. 5, No. 5, 1990, pp. 451–461.

Coleman, et al: Osteocalcin: a Potential Marker of Metastatic Bone Disease and Response to Treatment, European Journal of Cancer & Clinical Oncology, vol. 24, No. 7, pp. 1211–1217, Jul. 1988.

Diaz Diego, et al: "Six Osteocalcin Assays Compared", Clinical Chemistry, vol. 40, No. 11, 1994, pp. 2071–2077.

Banfi, et al: "In Vitro stability of Osteocalcin", Clinical Chemistry, vol. 40, No. 5, 1994, pp. 833–834.

Primary Examiner—Ponnathapura Achutamurthy
Attorney, Agent, or Firm—Cushman Darby & Cushman IP Group for Pillsbury Madison & Sutro LLP

[57] ABSTRACT

Progressive degradation of the osteocalcin present in the blood, serum or plasma samples obtained from a patient is observed in such samples and leads to falsification of the osteocalcin values obtained in a subsequent determination. It has been found that this osteocalcin degradation can be prevented by adding an amount of divalent metal ions, in particularly calcium ions, sufficient to prevent osteocalcin degradation to the sample immediately after it has been obtained or while it is being obtained.

8 Claims, 3 Drawing Sheets

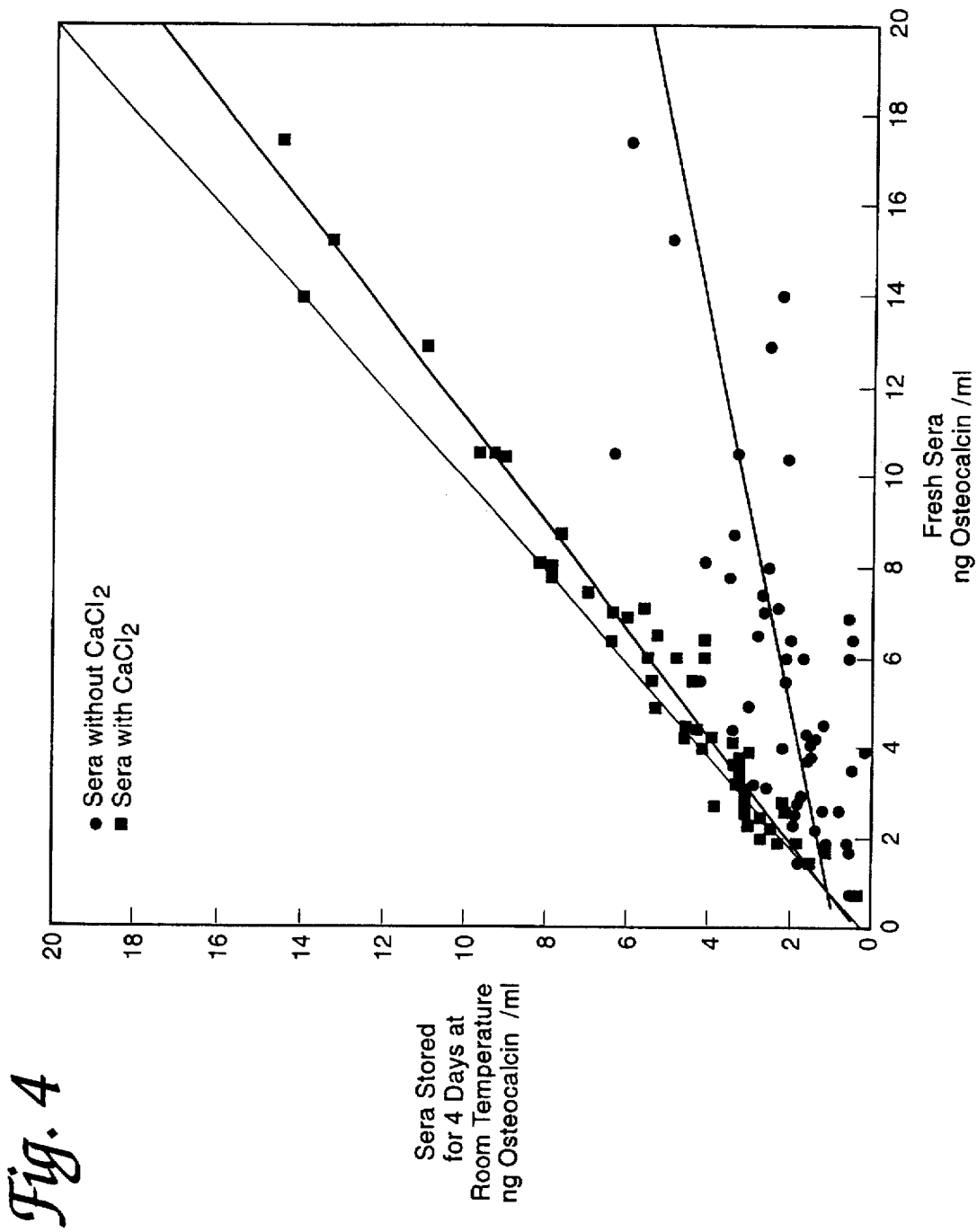

METHOD FOR STABILIZING OSTEOCALCIN IN HUMAN SERUM OR PLASMA SAMPLES FOR THE DETERMINATION OF THE OSTEOCALCIN CONTENT THEREIN, AND INSTRUMENTS AND SAMPLE VESSELS FOR CARRYING OUT SAID METHOD

This application claims benefit of international application PCT/EP94/03962, filed Nov. 29, 1994.

The invention relates to a method for the determination of osteocalcin in human serum or plasma and instruments and sample vessels for carrying out this method. The method according to the invention may also be referred to as a method for stabilization of endogenous osteocalcin in human serum or plasma samples, since it is based on prevention of the degradation of the endogenous osteocalcin which is normally to be observed during the time between taking of the sample and measurement of the osteocalcin.

Human osteocalcin, which is also referred to as vitamin K-dependent bone protein or γ-carboxyglutamic acid-containing protein [bone Gla protein (BGP)], is a specific peptide component of the bone matrix. The peptide consists of 49 amino acids and has the following amino acid sequence: Tyr-Leu-Tyr-Gln-Trp-Leu-Gly-Ala-Pro-Val-Pro-Try-Pro-Asp-Pro-Leu-Glu-Pro-Arg-Arg-Gla-Val-Cvs-Gla-Leu-Asn- Pro-Asp-Cys-Asp-Glu-Leu-Ala-Asp-Arg-Ile-Gly-Phe-Gln-Glu-Ala-Tyr-Arg-Arg-Phe-Tyr-Gly-Pro-Val$^{49}$ The peptide is synthesised by the osteoblasts and a small part of the osteocalcin formed enters the blood. Certain valuable conclusions about the metabolism of the bone are possible through the determination of the concentration of this osteocalcin in the blood, and, for additional information, reference may be made to the article by Lian, J. B. and Gundberg, C. M. in: Clinical Orthopaedics and Related Research, 226, pages 267 to 291 (1988). According to this, the determination of the osteocalcin concentration in human serum or plasma may provide useful information for the diagnosis and therapy of metabolic disorders of the bone.

Various methods have been developed for measuring the osteocalcin concentration. Thus, according to methods known per se, the determination of the osteocalcin concentration is possible by an immunodiagnostic route, for example by the method according to U.S. Pat. No. 4,438,208 and the improved embodiment of such a method, described in German Patent 3,833,936 of the Applicant.

EP 0 557 663 A1 relates to an immunodiagnostic assay method wherein a very special monoclonal antibody for osteocalcin is used, which antibody recognizes certain conformations which are typical for the so-called non-carboxylated or under-carboxylated osteocalcin. Non-carboxylated or under-carboxylated osteocalcin is disguished over carboxylated osteocalcin by the fact that the initial GLU residues in the positions 17, 21 and 24 of the osteocalcin molecule are not or not completely carboxylated to form GLA residues. The different degree of carboxylation causes differences in the conformations of the two forms.

In order to be able to measure with a "conformational" antibody as used in the assay also the total amount of osteocalcin, i.e. to measure also the carboxylated osteocalcin present, a calcium salt is added to the sample, because it was found that in the presence of a calcium salt the conformation of the carboxylated osteocalcin changes so that the specific antibody recognizes also the carboxylated osteocalcin and binds to it for measurement purposes exactly as to the non-carboxylated or under-carboxylated osteocalcin. EP 0 557 663 A1 does not address the problem of stabilising osteocalcin during the period between the taking of the sample and the later immunodiagnostic determination.

Regardless of the method by which the osteocalcin concentration is determined, it is essential for a reliable and clinically relevant determination of the osteocalcin in the sample that the osteocalcin concentration measured reflects the concentration at the time of taking of the blood. Concentration changes in the period between taking of the blood and actual concentration measurement lead to useless results being obtained.

It is already known that endogenous osteocalcin in blood samples undergoes degradation (cf. Lian and Gundberg (1988) loc. cit and Coleman et al. (1988) Eur. J. Cancer Clin. Oncol. 24, 1211–1217). As a result of this, "falsely low" osteocalcin concentrations in the serum or plasma are found, depending on the method and duration of storage of the sample prior to the measurement. It has already been proposed to overcome this problem by freezing or freeze-drying sera/plasma samples immediately after they have been obtained and before storage. However, both methods are impractical (for example the transport of sera in the frozen state) or expensive and complicated (freeze-drying).

Immediate measurement of the osteocalcin concentration directly after taking of the sample is possible only in the rarest cases but on no account in normal medical practice, where it is usual to send the samples obtained from the patients to a laboratory for investigation.

It is therefore the object of the present invention to provide an improved method for the determination of osteocalcin in human serum or plasma, in which the degradation of the endogenous osteocalcin in the sample can be prevented and hence eliminated as a source of error, and in which no complicated, unusual technical measures have to be taken for sample stabilization.

This object is achieved by a method for the determination of osteocalcin in human serum according to the present invention wherein an amount of divalent metal ions, in particular calcium ions, sufficient to prevent osteocalcin degradation is added to the sample immediately after it has been obtained or while it is being obtained.

Advantageous embodiments of the method according to the invention are described herein.

Specially prepared instruments or sample vessels, as described in detail in below, may be used for carrying out the method according to the invention.

In providing the present invention, the approach was adopted of finding a substance which, when added to the serum or plasma, prevents the degradation of the endogenous osteocalcin.

The assumption, shared by Lian and Gundberg (loc. cit), that the degradation of the osteocalcin is proteolytic, that is to say is caused by proteases present in the serum and plasma, was used as a starting point. Hence, an attempt was initially made to suppress the osteocalcin degradation by adding suitable proteolysis inhibitors, for example those successfully used in the method according to German Patent 3,833,936 for preventing tracer degradation. It was found that it is not possible to reduce the degradation of the osteocalcin with the proteolysis inhibitors tested to date. When an attempt was then made to add the metal chelators EDTA and o-phenanthroline, which are also known proteolysis inhibitors, for inhibiting the osteocalcin degradation, surprisingly an acceleration of the osteocalcin hydrolysis was observed instead of inhibition.

Conclusions which permitted the provision of the method according to the invention were then drawn from this observation: if the accelerating effect of the metal chelators on the osteocalcin degradation is due to the fact that the metal ion concentration in the sample is reduced, this metal ion concentration is important for the degradability of the osteocalcin. An attempt was therefore made to achieve stabilization of the osteocalcin by increasing the metal ion concentration in the serum.

It was found that the addition of soluble calcium salts, for example of calcium chloride $CaC_2$, completely suppressed the degradation of osteocalcin if the added concentrations are correctly chosen. A series investigation was carried out for this purpose and showed that it was only above 20 mM $CaCl_2$ in the sample that no change in the osteocalcin concentration, detected on the basis of the osteocalcin immunoreactivity, was obtained.

Evidently, as a result of the addition of calcium ions and other divalent metal ions acting similarly to calcium ions, the osteocalcin is converted into a state in which it is no longer degradable by the proteases present, without losing the immunoreactivity essential for its detection by an immunodiagnostic method.

Suitable metal ions which act identically or similarly to calcium ions are in particular divalent metal ions and among these especially magnesium ions, zinc ions and cobalt ions, but it is possible that, on the basis of the knowledge of the method according to the invention and by means of simple series tests, it is also possible to find further divalent or possibly trivalent metal ions which are effective for stabilising the osteocalcin concentration for the purposes of the method according to the invention.

It is also possible that certain substances which are known to act biochemically similarly to calcium ions can be successfully used for preventing osteocalcin degradation.

For obvious reasons, the metal ions should in principle be added as early as possible after obtaining the sample, in order to suppress the onset of osteocalcin degradation from the beginning in the sample obtained.

The metal ions can in principle be added in any form, provided that they dissolve to a sufficient extent in the sample. Thus, they may be added in the form of soluble solid salts or in the form of solutions in aqueous or water-miscible solvents, provided that the solvents used do not interfere with the subsequent measurement.

In practice, the method according to the invention can be advantageously realised in various ways. Thus, substances and/or prepared sample vessels may be added to kits for osteocalcin determination. For example, the required calcium concentrations may be included in the form of calcium tablets.

However, since the stabilization has to be effected at the time of obtaining the sample, while the actual measurement is carried out at a completely different place, it is advantageous for the sampling to be carried out in daily medical practice if special instruments or sample vessels for osteocalcin determination are made directly available to the doctor. Thus, the doctor can be provided with calcium tablets in the correct dosage for sample stabilization, but he may also be provided with specially prepared instruments, such as, for example, blood-taking syringes or special vessels for the storage and despatch of the samples, which contain the required metal concentrations in suitable form from the onset. One possibility for the preparation of such instruments or sample vessels which appears advantageous consists in applying to the wall a solid film which is soluble in the sample, contains the metal ions and releases them into the sample. This film may be exclusively a dried-on salt film but may also contain a neutral binder soluble in the sample. The metal ions are used in the form of suitable water-soluble salts with tolerated anions. Thus, the preferred calcium ions can be successfully introduced in the form of calcium chloride. Poorly soluble or insoluble salts are as a rule unsuitable, as are salts whose anions are harmful to the stability of the sample or to the subsequent measurement, for example owing to an undesirable effect on the pH.

The method according to the invention is illustrated in detail below with reference to Experiments and Comparative Experiments.

BRIEF DESCRIPTION OF DRAWINGS

FIG. 4 shows the comparison of the osteocalcin degradation in serum samples with and without $CaCl_2$ (20 mM) on storage for 4 days at room temperature.

DESCRIPTION OF EXPERIMENT

The effect of different substances and added amounts on the serum samples and plasma samples with regard to the stabilization of the osteocalcin concentration in the samples was determined by determining the amounts of osteocalcin in the samples at different times and under different conditions with the aid of the OSCAtest Osteocalcin BGP (Henning Berlin GmbH).

The RIA used consisted of the following components:
test tubes coated with antiosteocalcin (37–49) antibodies (polyclonal, sheep)
a radiolabelled tracer (analog peptide N-acetyl-$^{125}$I-Tyr-Gln-Glu-Ala-Phe-Arg-Arg-Phe-Phe-Gly-Pro-Val) which was stabilised by the addition of leupeptin (cf. German Patent 3,833,936)
a standard series which was formed from human bone extract and human, osteocalcin-free serum.

RIA procedure:
50 µl of standard or 50 µl of patient's serum and 250 µl of tracer are pipetted into each of the test tubes. After incubation for 20–24 hours at 4° C., free tracer is separated from bound tracer by a washing step and the radioactivity remaining in the tube -is measured.

As is known from HPLC investigations, this RIA detects only the intact osteocalcin.

Figure 1:
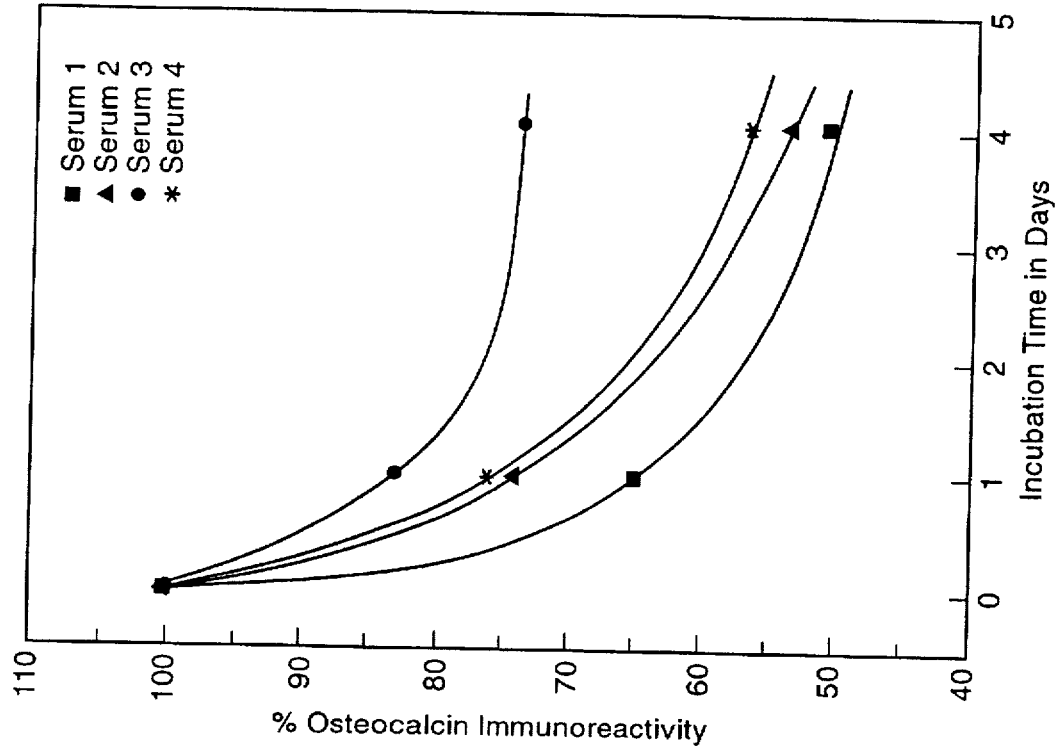
FIG. 1 shows a decrease in the osteocalcin concentration in four serum samples as a percentage decrease in the osteocalcin immunoreactivity in an RIA.

Typical results obtained as a result of osteocalcin degradation in the samples are shown in FIG. 1. The results shown in the Figure were obtained by incubating freshly taken sera at room temperature (25° C.) for the times shown in the graph. After the times shown, the degradation was terminated by freezing the samples. Osteocalcin was then determined in all samples in an assay by means of the RIA described above.

The curves show the variation in the osteocalcin immunoreactivity as a measure of the concentration of the intact osteocalcin in the samples for normal sera.

As is evident from FIG. 1, a substantial degradation of the osteocalcin (decrease of osteocalcin immunoreactivity) is obtained in all samples if sera are stored at 25° C. This degradation takes place at only a slightly reduced rate even at 4° C.

Experiment to inhibit osteocalcin degradation by adding proteolysis inhibitors

In order to decrease osteocalcin degradation due to proteases, an attempt was made to prevent osteocalcin degradation by adding proteolysis inhibitors (similarly to German Patent 3,833,936).

The following inhibitors were investigated with regard to their ability to reduce the osteocalcin degradation shown in FIG. 1, the inhibitor concentration at the time of incubation with serum being stated in parentheses after the substances tested:

amastatin (100 μM), bestatin (100 μM), leupeptin (100 μM), pepstatin (100 μM), elastatinal (100 μM), benzamidine (1 mM), phosphoramidone (1 mM), trasylol ($1.6 \times 10^6$ units/ml), heparin (5 mg/ml), trypsin inhibitor from soya beans (0.1 mg/ml), antithrombin III (0.1 unit/ml), N-ethylmaleimide (2 mM), p-chloromercuryphenylsulphonic acid (1 mM), diisopropyl fluorophosphate (1 mM), phenylmethylsulphonyl fluoride (2 mM), o-phenanthroline (5 mM) and ethylenediaminetetraacetic acid (EDTA) (10 mM).

None of these substances led to a reduction in the degradation of osteocalcin. In the case of the metal chelators EDTA and o-phenanthroline, an acceleration of the osteocalcin hydrolysis was actually observed.

Addition of calcium ions ($CaCl_2$)

Figure 2:
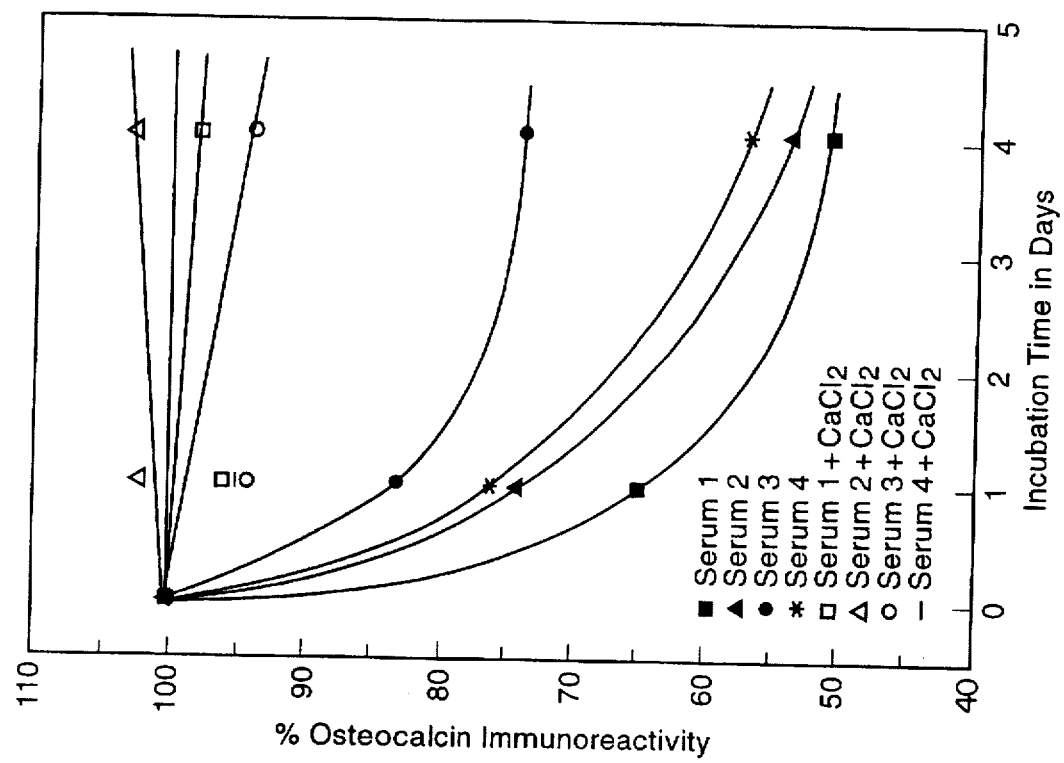
FIG. 2 shows the effect of the addition of $CaCl_2$ (20 mM) to samples corresponding to FIG. 1

When, instead of proteolysis inhibitors, $CaCl_2$ was added to the samples in an amount such that the concentration in the samples was 20 mM, it was found that the degradation of osteocalcin was completely suppressed. The results are shown in FIG. 2.

As can be seen, the osteocalcin immunoreactivity remains unchanged over a period of 4 days when $CaCl_2$ is added to the sample.

In order to determine the calcium concentration which must be added as the minimum concentration to protect osteocalcin completely, the effect of various $CaCl_2$ concentrations on the degradation of osteocalcin was investigated. For this purpose, 5, 10, 20 and 40 mM were added to sera which were then incubated for 4 days at 25° C., after which the residual osteocalcin was determined.

It was found that no further change in the osteocalcin immunoreactivity of the sera could be detected above an added amount corresponding to about 20 mM $CaCl_2$. From this it may be concluded that calcium ions in a concentration of at least 20 mM must be added to the sera in order to keep the endogenous osteocalcin stable for at least 4 days at 25° C.

To check the stabilization effect due to the addition of calcium ions by another method and at the same time to ensure that the stabilising addition of calcium ions does not result in changes in the immunoreactivity of the test components, which cast doubt on the value of the immunodiagnostic determination of osteocalcin, identical sera were determined in the double determination in the OSCAtest BPG of the Applicant, on the one hand as fresh sera and on the other hand after storage for four days at 25° C. with and without the addition of $CaCl_2$. The results are shown in FIG. 4. As can be seen, the deviation from a straight line at an angle of 45°, which would imply complete identity of the measured results for the fresh sera and the stored sera, is virtually negligible for the sera stabilised with $CaCl_2$. The correlation coefficients were 0.98 (with $CaCl_2$) and 0.64 (without $CaCl_2$) and the mean recovery was 94% and 47%, respectively.

Checking the stabilization effect using a different assay method for osteocalcin In order to ensure that the results obtained above are generally valid and are not dependent on the specific RIA method used, the measurement of the degradation of osteocalcin was repeated by means of the commercial osteocalcin RIA from Isotopen Diagnostik CIS GmbH.

Figure 3:
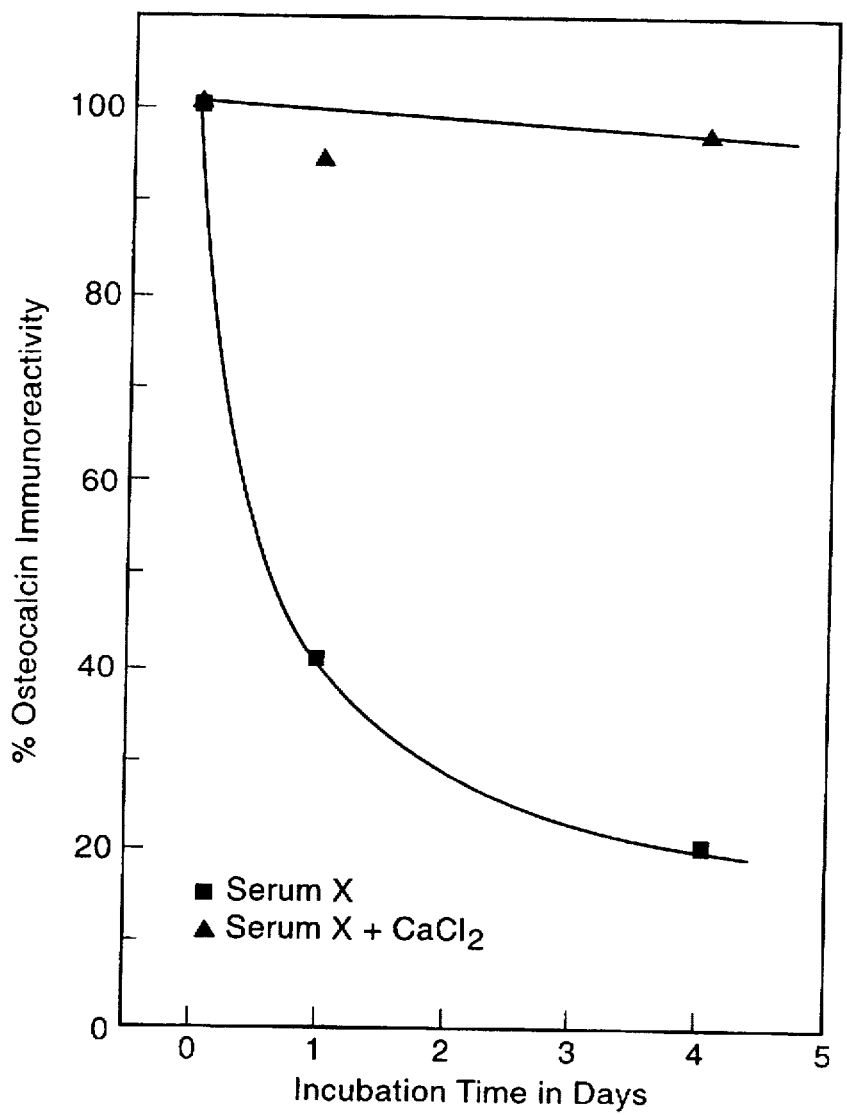
FIG. 3 shows the effect of the addition of $CaCl_2$ (20 mM) to samples in which the osteocalcin concentration was determined as the percentage residual osteocalcin immunoreactivity in a commercial RIA other than that in FIG. 1 and 2.

Freshly obtained sera were incubated for the times shown in FIG. 3 in the presence or absence of $CaCl_2$ (20 mM) at 25° C. The determination of the residual osteocalcin concentration by means of the stated RIA showed that the decrease in the osteocalcin concentration could be prevented by the addition of $CaCl_2$.

To investigate the degradation of osteocalcin by another method, a further experiment was carried out:

Radioiodinated bovine osteocalcin 1–49 ($1 \times 10^6$ cpm) was incubated with human serum (300 μl), with and without $CaCl_2$ (48 hours, 25° C.). The reaction mixture was then analyzed by HPLC.

The separation column used was a μBondapak $C_{18}$ column from Waters. The column was equilibrated in mobile phase A (water:acetonitrile:trifluoroacetic acid) (95:5:0.1) (V/V/V). After application of the sample, elution was carried out in a gradient of mobile phase A and mobile phase B (water : acetonitrile trifluoroacetic acid) (10:90:0.1) (V/V/V): in 3 min linearly from 100/0 A/B to 85/15 A/B, linearly in 37 min to 20/80 A/B and then in 5 min linearly to 0/100 A/B. The flow rate was 1 ml/min. The radioactivity of the column outflow was detected continuously by means of a Ramona radioactivity monitor (from Raytest).

Result:

In addition to the bovine osteocalcin (elution time: 17.1 min), further peaks (elution times 2.4, 7.2 and 9.5 min) were observed but could be completely suppressed by the addition of 20 mM $CaCl_2$.

The results show that the degradation of bovine osteocalcin can be completely prevented with the addition of 20 mM $CaCl_2$.

We claim:

1. A method for preventing the degradation of osteocalcin in human serum or plasma samples wherein an amount of divalent metal ions sufficient to prevent osteocalcin degradation is added to the sample immediately after or while said sample is obtained.

2. A method according to claim 1, wherein divalent metal ions selected from the group consisting of calcium ions, magnesium ions, zinc ions and cobalt (II) ions are added.

3. A method according to claim 1, wherein calcium ions are added to the sample in an amount such that the calcium concentration in the sample increases by at least 20 mM.

4. A method according to claim 1, wherein the divalent metal ions are added to the sample in the form of solid salts or as aqueous solutions.

5. A method according to claim 1, wherein the divalent metal ions are added to the sample by previously placing them in the instruments used for obtaining the sample or in the sample vessels.

6. A method according to claim 1, wherein the divalent metal ions are added in the form of a tablet which contains an amount of metal ions adjusted to the sample volume.

7. An instrument or sample vessel suitable for obtaining blood samples and for storing and processing said samples to serum samples or plasma samples wherein said instrument or sample vessel contains an amount of divalent metal ions in liquid or solid form sufficient to prevent osteocalcin degradation of osteocalcin in said blood samples.

8. An instrument or sample vessel according to claim 7, wherein said metal ions are in the form of a solid film on an inner wall of said instrument or sample, which film is soluble in said blood sample.

* * * * *